United States Patent [19]

Goel

[11] Patent Number: 4,761,466

[45] Date of Patent: Aug. 2, 1988

[54] INIDAZOLINE THIOCYANATES AS CURE ACCELERATORS FOR AMINE CURING OF EPOXIDE RESINS

[75] Inventor: Anil B. Goel, Worthington, Ohio

[73] Assignee: Ashland Oil, Inc., Ashland, Ky.

[21] Appl. No.: 84,351

[22] Filed: Aug. 12, 1987

[51] Int. Cl.$^4$ ............................................. C08G 59/68
[52] U.S. Cl. ....................................... 528/90; 528/94;
528/109; 528/361; 528/407
[58] Field of Search ................... 528/90, 94, 109, 361, 528/407

[56] References Cited

U.S. PATENT DOCUMENTS

| 3,642,649 | 2/1972 | Green et al. | 548/335 X |
| 3,660,354 | 5/1972 | Uelzmann | 528/90 X |
| 3,763,098 | 10/1973 | Green et al. | 528/90 |
| 4,161,575 | 7/1979 | Seymour et al. | 528/94 X |

Primary Examiner—Earl Nielsen
Attorney, Agent, or Firm—John F. Jones

[57] ABSTRACT

An adhesive composition comprising a mixture of a polyepoxide, an amine curing agent and a thiocyanate salt of a compound having the formula

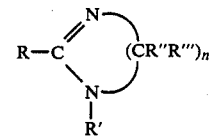

wherein R represents an alkyl group having from 1 to 20 carbon atoms, an aryl group having from 6 to 20 carbon atoms or an alkaryl group having from 7 to 20 carbon atoms, R', R" and R''' independently represent hydrogen, an alkyl group having from 1 to 10 carbon atoms or an alkyl ether group having from 1 to carbon atoms and n represents 2 or 3 is described.

14 Claims, No Drawings

INIDAZOLINE THIOCYANATES AS CURE ACCELERATORS FOR AMINE CURING OF EPOXIDE RESINS

This invention relates to a process for the acceleration of cure of mixtures of epoxy resins and amine hardeners comprising including in said mixtures a thiocyanate salt of an imidazoline or a thiocyanate salt of an imidazine as cure accelerator.

A variety of aromatic and aliphatic polyamines (primary, secondary amines, mixed primary and secondary amines and combinations of these with tertiary amines) and amido amines therefrom have been used extensively as curing agents for epoxy resins. In order to improve the cure rate of the polyamine/epoxy resin mixtures, various types of cure accelerators (including tertiary amine group containing materials, phenolics, quaternary ammonium salts of strong acids and carboxylic acids, metal salts of carboxylic acids, boron trifluoride-amine complexes, boron trifluoride-phenol complexes, mercaptans, thioether alcohols and thiocarbamic acids) have been used in the prior art. (See article by Mika in "Epoxy Resins Chemistry and Technology," edited by May and Tanaka, Marcel Dekker, Inc., New York, 1973). For instance, U.S. Pat. Nos. 3,265,664 and 3,271,350 describe the use of guanamine, U.S. Pat. Nos. 3,291,776 and 3,821,166 describe the use of thioethers and mercaptans. U.S. Pat. No. 3,637,591 describes the use of neutral esters of a phosphorus acid. U.S. Pat. No. 2,909,494 describes the use of boron trifluoride-amine complexes. U.S. Pat. No. 4,554,342 describes the use of a trihydrocarbyl sulfonium salts. U.S. Pat. No. 4,110,313 describes the use of dithiocarbamate salt and U.S. Pat. No. 4,195,153 describes the use of an amino alcohol as an accelerator for the amine curing of epoxy resins. U.S. Pat. No. 3,903,048 describes the use of dimethyl dithiocarbamic acid dimethyl ammonium salt, bis(dimethyl thiocarbamyl) sulfide, tetramethylthiuram disulfide and the like as catalyst systems for lowering epoxy resin cure temperatures when cured with dicyandiamide.

The use of a tertiary amine salt of thiocyanic acid as an amine cure accelerator has been shown in U.S. Pat. Nos. 3,642,649 and 4,161,575. Quaternary ammonium (tetraalkylammonium) thiocyanate as accelerators for epoxy resins has been shown in U.S. Pat. No. 3,660,354. The use of alkali and alkaline earth metal thiocyanate salts with aminoethylpiperazine as a curing agent for epoxy resins has been shown in Japanese Patent No. 597823 (Chem Abstracts 101 (20) 172392z). Similarly, epoxy curing with polyamine/thiourea has been made in Japanese Patent No. 48092437.

Thus, it is quite apparent that the rapid curing of epoxy resins has been the subject of great industrial interest. Although the prior art cure accelerators improve the cure speed of epoxy resins cured with amine curing agents, these are associated with some limitations. For instance, accelerators such as mercaptans and thioethers have unpleasant odors. Certain accelerators such as boron trifluoride-amine complexes and boron trifluoride-phenol complexes are corrosive and esters of phosphorus acid and metal carboxylates such as stannous octoate are moisture sensitive. Some of the accelerators are not very efficient and promote acceleration only mildly. The use of products of the reaction of imidazolines with ammonium thiocyanate as cure accelerators in apoxide resin/amine systems has not been previously disclosed.

An objective of this invention is to provide a new class of cure accelerators which are free from the above described limitations associated with the prior art accelerators and which provide high cure acceleration of the amine curing of epoxy resins.

I have discovered that the reaction products of ammonium thiocyanate and an imidazolines function as excellent cure accelerators for the curing of epoxy resin/amine mixtures. The imidazolines (5-membered ring compounds) and imidazines (six-membered ring compounds) useful in this invention include those having the formula I

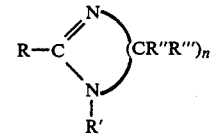

wherein R represents an alkyl group having from 1 to 20 carbon atoms, an aryl group having from 6 to 20 carbon atoms or an alkaryl group having from 7 to 20 carbon atoms, R', R" and R"' independently represent hydrogen, an alkyl group having from 1 to 10 carbon atoms or an alkyl ether group having from 1 to 10 carbon atoms and n represents 2 or 3.

Epoxy resins or polyepoxides useful in the practice of this invention include those disclosed in U.S. Pat. Nos. 2,500,600 and 2,324,483 which are incorporated herein by reference. Preferred in this invention are 1,2-epoxy compounds having an epoxide equivalence greater than 1, that is to say, compounds having more than one group of the formula:

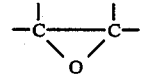

The 1,2-epoxide groups may be either terminal or inner ones. Particularly suitable terminal 1,2-epoxide groups are 1,2-epoxy ethyl or 1,2-epoxy propyl groups. The latter may be linked to an oxygen atom, that is to say, they are glycidyl ether or glycidyl ester groups. Compounds with inner epoxide groups usually contain the 1,2-epoxide group in an aliphatic chain or in a cycloaliphatic ring.

As epoxy compounds containing an inner 1,2-epoxy group there are suitable epoxidized diolefins, dienes, or cyclic dienes, such as 1,2,5,6-diepoxy hexane, 1,2,4,5-diepoxy cyclohexane, dicyclopentadiene diepoxide, dipentene diepoxide, vinyl cyclohexene diepoxide, epoxidized diolefinically unsaturated carboxylic acid esters, such as methyl-9,10,11,12-diepoxyhexadecane-1,16-dicarboxylic acid. Furthermore, there may be mentioned epoxidized mono-, di-, or polyesters and mono-, di-, or polyacetals containing at least one cycloaliphatic 5-membered or 6 membered ring, to which at least two 1,2-epoxidized groups are linked.

A widely used class of polyepoxides which can be used in the present invention are the epoxy polyethers obtained by reacting a halogen containing epoxide or dihalohydrin, such as epichlorohydrin, epibromohydrin, 3-chloro-1,2-epoxyoctane, and the like with either a polyhydric phenol or a polyhydric alcohol.

When ammonium thiocyanate is mixed with an imidazoline or imidazine, ammonia evolution occurs. This ammonia displacement reaction proceeds rapidly at elevated temperatures. The thiocyanate salts of imidazolines (five membered heteronuclear compounds with one C=N group) and imidazines (six membered heteronuclear compounds with one C=N group) may also be prepared by the reaction of imidazolines or imidazines with thiocyanic acid.

Although various thiocyanate salts have been used as cure accelerators, the use of imidazoline and imidazine thiocyanates, which are chemically quite different from the prior art salts, has never been made in the prior art. Imidazoline or imidazine thiocyanate salts, which are quite convenient to use because of their excellent solubility properties, have been generally found to be more effective than the prior art cure accelerators.

The stoichiometric reaction of one ammonium thiocyanate mole per imidazoline or imidazine group results in products which show strong infrared spectral bands at 2060 cm$^{-1}$, indicating the presence of thiocyanate groups and also broad bands in the region of 2400 cm$^{-1}$ to 2800 cm$^{-1}$, indicating the products to be amine salts. These salts when added to the epoxy compositions containing amines and amido amine curing agents which may also contain other known accelerators such as phenolics, mercaptans and other thio group containing accelerators described in the prior art, cure rapidly at ambient temperature as well as at low-to moderately elevated temperatures from about room temperature to about 150° C., although higher temperatures can also be used.

The catalysts of this invention accelerate the curing of epoxy resin-amine mixtures to such an extent that small amounts from about 0.2 to 20% by weight of the total epoxy resin composition and preferably from about 1 to 10% by weight are needed to reduce the cure time several fold. For instance, the reaction of a mixture of a liquid diglycidyl ether of Bisphenol-A with 20% by weight of aminoethylpiperazine, based on the weight of the total mixture, which required about 50 minutes at room temperature to give a gelled product, when carried out in the presence of about 5% by weight of the total epoxy resin/amine mixture of the thiocyanate complex of an imidazoline of formula I wherein R is methyl, R' and R" are hydrogen and R'" is a methyl group and n is 2, prepared by reaction of a 1:1 mole ratio of the imidazoline with ammonium thiocyanate, the curing occurs within four minutes of mixing at room temperature or about 12 times the rate of the uncatalyzed mixture.

The amine curing agents useful in the present invention include mono-, di-, and polyamines containing primary amine, secondary amine, mixed primary and secondary amine and combinations of these with tertiary amines and the amido amines obtainable from these amines by the amidation reaction with carboxylic acids. The amines and amido amines may also contain other functionalities such as hydroxyl groups and other groups such as ether, thioether, urea and the like in the backbone. Typical of such amines are butyl amine, dodecylamine, triethylamine, triethylene diamine, cyclohexylamine, ethylene diamine, dipropylene triamine and the like, cyclohexane dimethyl diamine, hexamethylene diamine, isophorone diamine, xylene diamine, aminoethylpiperazine, bis(amino propyl) piperazine, piperidine, piperazine, morpholine, N-alkylpiperidines and N-alkyl-morpholines, dimer acid diamine, bis-(amino methyl) cyclohexane, aromatic polyamines, alkanol amines such as ethanolamine, diethanolamine, triethanolamine, N-substituted alkanol amines, poly-(alkylene ether) polyamines, melamine, and the like and poly (oxy alkylene) polyamines having molecular weights ranging from 200 to 10,000 such as poly(oxy propylene) triamine and others disclosed in U.S. Pat. Nos. 3,235,895; 3,654,370 and 3,666,788. The catalysts of this invention in combination with amines, amido amines (reaction products of carboxylic acid with an amine) and amines with phenolics and mercaptans, may be used in epoxy resin formulations useful in applications such as coatings, adhesives, RIM, reinforced plastics, composites, potting compounds, tooling compounds, injection molding, SMC, and the like. The catalyt may be dissolved or dispersed in the amine hardener and if desired, may be encapsulated in either thermoplastic materials or by reacting with reactive molecules such as isocyanate, epoxide and other techniques known in the art. The curable compositions of this invention may also include additives such as plasticizers, diluents, solvents, fillers, antioxidants, colorants and the like.

This invention is further illustrated in the following representative examples.

EXAMPLE 1

The thiocyanate complex of an imidazoline of formula I wherein R is methyl, R' and R" are hydrogen, R'" is methyl and n is 2 (3.8g) and 3.0g of powdered ammonium thiocyanate were mixed and heated at 110 degrees C. for 30 minutes during which time ammonia gas evolution was observed. The resulting liquid was degassed under reduced pressure to remove dissolved ammonia. The infrared spectrum of the product showed a strong band at 2060 cm$^{-1}$ indicating the presence of the thiocyanate group. This material was used as cure accelerator in the amine curing of epoxy resins. Typically, 0.5g of this accelerator was mixed with 2.5g of aminoethylpiperazine and the resulting mixture was added to 12 g of liquid diglycidyl ether of Bisphenol-A (DGEBPA, epoxy equivalent weight of 180–190). The resulting mixture gelled in four minutes at room temperature.

EXAMPLE 2

This example is for comparative purposes and is outside the scope of this invention. Aminoethylpiperazine (3.0g) was mixed with 12g of DGEBPA at room temperature. The gel time of the mixture was found to be 51 minutes. In another experiment, 12g of DGEBPA was mixed with 2.5g of aminoethylpiperazine and 0.4g of the imidazoline described in Example 1. The room temperature gel time of the mixture was found to be 50 minutes. In another experiement, 10g of DGEBPA was mixed with 0.5g of the imidazoline of Example 1. The resulting mixture took more than five hours to gel at room temperature. These experiments show that the amine hardener itself or amines with the imidazoline alone do not cure epoxy resins at a rate approaching that obtained when the thiocyanate complex accelerators of this invention are used.

EXAMPLE 3

The procedure of Example 1 was followed to prepare a thiocyanate complex by mixing 3.8g of an imidazine having the formula

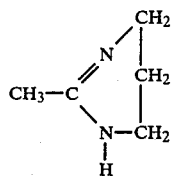

with 3g of ammonium thiocyanate. A 0.5g portion of this complex was mixed with 2.5g of aminoethylpiperazine to give a hardener which was then allowed to react with 12g of DGEBPA at room temperature. Gelation occurred in six minutes to give a solid thermoset polymer. In comparison, when 12g of DGEBPA was mixed with 2.5g of aminoethylpiperazine and 0.5g of the imidazine, the gel time at room temperature was 37 minutes.

EXAMPLE 4

The procedure of Example 1 was followed using 12g of DGEBPA, 2.5g of triethylene tetramine and 0.5g of the thiocyanate complex catalyst of the imidazoline. The mixture gelled at room temperature in 14 minutes to give a solid polymer. In comparison, a solution of 12g of DGEBPA, 2.5g of triethylene tetramine and 0.4g of the imidazoline of Example 1 required 65 minutes to gel at room temperature.

EXAMPLE 5

The procedure of Example 1 was followed using 12g of DGEBPA, 2.5g of diethylene triamine and 0.5g of the thiocyanate complex of the imidazine of Example 3. The room temperature gel time was 13 minutes for the resulting mixture. In comparison, the room temperature gel time for a mixture of 12g of DGEBPA, 2.5g of diethylene triamine and 0.4g of the imidazine of Example 3 was found to be 56 minutes.

EXAMPLE 6

A thiocyanate complex of an imidazoline was prepared by following the procedure of Example 1 using 3.5g of an imidazoline of formula

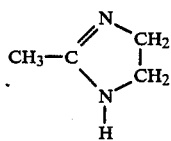

and 3g of ammonium thiocyanate. The resulting catalyst (0.5g) was mixed with 1.0g of aminoethylpiperazine and 3g of poly (oxypropylene) triamine (molecular weight of 400) and this hardener was mixed with 10g of DGEBPA. The resulting mixture gelled at room temperature in 12 minutes. Some of the mixture before gelling was applied to the surface of a zinc phosphatized steel plate in the form of a 1 mil thick coating and this was cured at 100 degrees C. for 10 minutes. The resulting very glossy, non-tacky coating (film), was found to have a 2H pencil hardness (ASTM D-3363) and it showed 100% adhesion (Tape Adhesion test, ASTM D-3359) and a reverse impact strength (ASTM D-2794) of greater than 80 inches/pound.

EXAMPLE 7

The procedure of Example 1 was followed using 10g of DGEBPA, 1g of the diglycidyl ether of poly (oxpro-pylene) glycol (epoxy equivalent weight of 320), 1g of aminoethylpiperazine, 2.5g of an amido amine obtained by the amidation reaction of linoleic acid (reactive proton equivalent weight of 90) and diethylene triamine and 0.5g of the thiocyanate salt of Example 1. The resulting mixture was found to cure at room temperature in eight minutes to give a thermoset polymer.

EXAMPLE 8

The thiocyanate catalyst of an imidazoline was prepared by reacting equimolar amounts of ammonium thiocyanate and an imidazoline of formula

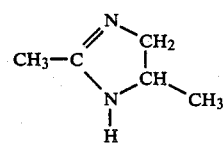

at 110° C. for 30 minutes and removing the ammonia byproduct. A mixture of 0.5g of this catalyst and 4g of poly(oxypropylene) triamine (400 molecular weight) was mixed with 8g of the diglycidyl ether of Bisphenol-A. Part of the resulting solution was applied to a zinc phophatized steel plate in the form of A 1-2 mils thick coating. The coating was cured at 110° C. in an oven for 10 minutes. The remaining part of the solution gelled at 100° C. in 3 minutes. The cured coating on steel had a pencil hardness of H and showed 100% adhesion (tape adhesion test) and reverse impact strength of greater than 100 inch pounds showing the film to be tough and flexible.

I claim:

1. An adhesive composition comprising a mixture of a polyepoxide, an amine curing agent and a thiocyanate salt of a compound having the formula

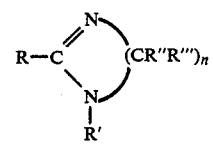

wherein R represents an alkyl group carbon atoms, an aryl group having from 6 to 20 carbon atoms or an alkaryl group having from 7 to 20 carbon atoms, R', R" and R'" independently represent hydrogen, an alkyl group having from 1 to 10 carbon atoms or an alkyl ether group having from 1 to 10 carbon atoms and n represents 2 or 3.

2. The composition of claim 1 wherein the polyepoxide is a compound having more than one group of the formula

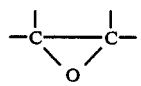

3. The composition of claim 2 wherein the thiocyanate salt is present in from about 0.2 to 20% by weight of the mixture.

4. The composition of claim 3 wherein the amine curing agent is selected from the group consisting of butyl amine, dodecyl amine, triethyl amine, triethylene diamine, cyclohexylamine, ethylene diamine, dipropylene triamine, cyclohexane dimethyl diamine, hexamethylene diamine, xylene diamine, isophorone diamine, aminoethylpiperazine, bis (amino propyl) piperazine, piperidine, morpholine, N-alkyl piperidines, N-alkyl morpholines, dimer acid diamine, bis (amino methyl) cyclohexane, aromatic poly amines, ethanolamine, diethanolamine, triethanolamine, N-substituted alkanol amines, poly (alkylene ether) polyamines, melamine, and poly (oxy alkylene) polyamines having molecular weights ranging from 200 to 10,000.

5. The composition of claim 4 wherein the compound is one in which R represents a methyl group, R' and R'' represent hydrogen, R''' represents a methyl group and n represents 2.

6. The composition of claim 5 wherein the polyepoxide is the diglycidyl ether of Bisphenol-A and the amine curing agent is aminoethylpiperizine.

7. The composition of claim 4 wherein the compound is of the formula

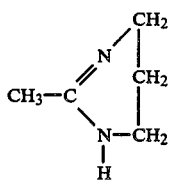

8. The composition of claim 7 wherein the polyepoxide is the diglycidyl ether of Bisphenol-A and the amine curing agent is aminoethylpiperizine.

9. The composition of claim 5 wherein the polyepoxide is the diglycidyl ether of Bisphenol-A and the amine curing agent is diethylene triamine.

10. The composition of claim 4 wherein the compound is one of formula

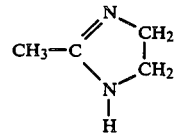

11. The composition of claim 10 wherein the polyepoxide is the diglycidyl ether of Bisphenol-A and the amine curing agent is aminoethylpiperazine.

12. The composition of claim 5 wherein the polyepoxide is the diglycidyl ether of poly (oxypropylene) glycol and the amine curing agent is aminoethylpiperazine.

13. The composition of claim 4 wherein the compound is one of formula

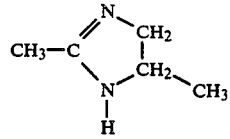

14. The composition of claim 13 wherein the polyepoxide is the diglycidyl ether of Bisphenol-A and the amine curing agent is poly (oxypropylene) triamine.

* * * * *